(12) United States Patent
Yu et al.

(10) Patent No.: US 11,293,895 B2
(45) Date of Patent: Apr. 5, 2022

(54) GAS SENSITIVE FIELD EFFECT TRANSISTORS

(71) Applicant: The Hong Kong University of Science and Technology, Hong Kong (CN)

(72) Inventors: Qian Yu, Hong Kong (CN); Amine Bermak, Hong Kong (CN); Chi Ying Tsui, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 118 days.

(21) Appl. No.: 16/439,215

(22) Filed: Jun. 12, 2019

(65) Prior Publication Data
US 2019/0383769 A1 Dec. 19, 2019

Related U.S. Application Data

(60) Provisional application No. 62/763,340, filed on Jun. 13, 2018.

(51) Int. Cl.
*H01L 29/788* (2006.01)
*H01L 29/66* (2006.01)
(Continued)

(52) U.S. Cl.
CPC ....... *G01N 27/4141* (2013.01); *G01N 27/127* (2013.01); *G01N 27/414* (2013.01);
(Continued)

(58) Field of Classification Search
CPC ........... G01N 27/4141; G01N 27/4148; G01N 27/4146; G01N 27/127; G01N 33/0031; H01L 29/788; H01L 29/66825
See application file for complete search history.

(56) References Cited

U.S. PATENT DOCUMENTS 5,918,110 A   6/1999   Abraham-Fuchs et al.
7,772,617 B2  8/2010   Fleischer et al.
(Continued)

OTHER PUBLICATIONS

Meile Wu, Jongmin Shin, Yoonki Hong, Dongkyu Jang, Xiaoshi Jin, Hyuck-In Kwon, Jong-Ho Lee; An FET-type gas sensor with a sodium ion conducting solid electrolyte for CO2 detection, Sensors and Actuators B: Chemical, vol. 259, 2018, pp. 1058-1065, ISSN 0925-4005 (Year: 2017).*

(Continued)

*Primary Examiner* — Aaron J Gray
(74) *Attorney, Agent, or Firm* — Amin, Turocy & Watson, LLP (57) ABSTRACT

Aspects describe gas sensitive field effect transistor (FET) structures, a gas sensitive FET array including the disclosed gas sensitive FET structures, and methods of manufacturing and using the same. In one example, a gas sensitive FET structure can include a body comprising a substrate layer, an intermediate layer over the substrate layer, and a passivation layer over the intermediate layer. Primary terminals disposed within the body can include at least one source terminal, at least one drain terminal and at least one gate terminal. A floating gate disposed within the body can comprise metal at a top surface of the intermediate layer. The passivation layer can be etched over the floating gate, and the floating gate can be electrically coupled to the gate terminal of the primary terminals. A sensing material layer can be positioned over the floating gate. A reset element can be included for resetting the floating gate.

20 Claims, 7 Drawing Sheets

(51) Int. Cl.
  *G01N 27/414* (2006.01)
  *G01N 33/00* (2006.01)
  *G01N 27/12* (2006.01)
(52) U.S. Cl.
  CPC ..... *G01N 27/4146* (2013.01); *G01N 27/4148* (2013.01); *G01N 33/0031* (2013.01); *H01L 29/66825* (2013.01); *H01L 29/788* (2013.01)

(56) References Cited

U.S. PATENT DOCUMENTS

| | | | |
|---|---|---|---|
| 9,903,834 B2 | 2/2018 | Lee et al. | |
| 9,964,515 B2 | 5/2018 | Rothberg et al. | |
| 2005/0230271 A1* | 10/2005 | Levon | G01N 27/4148 205/789 |
| 2011/0169056 A1* | 7/2011 | Wey | H01L 29/4958 257/253 |
| 2011/0227061 A1* | 9/2011 | Lee | B82Y 40/00 257/43 |
| 2011/0299337 A1* | 12/2011 | Parris | H01L 27/11558 365/185.18 |
| 2014/0131774 A1* | 5/2014 | Lee | G01N 27/4143 257/253 |
| 2016/0187279 A1* | 6/2016 | Tayebi | G01N 27/123 73/23.21 |

OTHER PUBLICATIONS

Yu et al., "Room-Temperature Dual-mode CMOS Gas-FET Sensor for Diabetes Detection", IEEE International Symposium on Circuits and Systems, 2018, 4 pages.

Tzeng et al., "A Portable Micro Gas Chromatography System for Lung Cancer Associated Volatile Organic Compound Detection", IEEE Journal of Solid-State Circuits, vol. 51, No. 1, Jan. 2016, pp. 259-272.

Sasago et al., "FET-type hydrogen sensor with short response time and high drift immunity", IEEE Symposium on VLSI Technology Digest of Technical Papers, 2017, pp. T106-T107.

Wu et al., "Pulse Biasing Scheme for the Fast Recovery of FET-Type Gas Sensors for Reducing Gases", IEEE Electronic Device Letters, vol. 38, No. 7, Jul. 2017, pp. 971-974.

Tang et al., "A 0.5V 1.27mW Nose-on-a-Chip for Rapid Diagnosis of Ventilator-Associated Pneumonia", IEEE International Solid-State Circuits Conference, Session 24, Integrated Biomedical Systems, 24.5, 2014, pp. 420-422.

Zanjani et al., "3D integrated monolayer graphene—Si CMOS RF gas sensor platform", npj, 2D Materials and Applications, vol. 1, No. 36, Oct. 26, 2017, pp. 1-9.

Hong et al., "Highly selective ZnO gas sensor based on MOSFET having a horizontal floating-gate", Sensors and Actuators B: Chemical, vol. 232, Sep. 2016, pp. 653-659.

Kim et al., "A New Gas Sensor Based on MOSFET Having a Horizontal Floating-Gate", IEEE Electron Device Letters, vol. 35, No. 20, Feb. 2014, pp. 265-267.

Kao et al., "A Sub-ppm Acetone Gas Sensor for Diabetes Detection Using 10 nm Thick Ultrathin InN FETs", Sensors, vol. 12, No. 6, May 29, 2012, pp. 7157-7168.

Wilbertz et al., "Suspended-Gate- and Lundstrom-FET integrated on a CMOS-chip", Sensors and Actuators A, 123-124, Sep. 23, 2005, pp. 2-6.

Josowicz et al., "Suspended Gate Field Effect Transistor Modified with Polypyrrole as Alcohol Sensor", Analytical Chemical, vol. 58, No. 3, Mar. 1986, pp. 514-517.

Barillaro et al., "An Integrated CMOS sensing chip for NO2 detection", Sensors and Actuators B: Chemical, vol. 134, No. 2, Sep. 25, 2008, pp. 585-590.

Guo et al. "A monolithic integrated 4 • 4 tin oxide gas sensor array with on-chip multiplexing and differential readout circuits" Solid-State Electronics 51 (2007) 69-76, 8 pages.

Eisele et al. "Low Power Gas Detection with FET Sensors" Sensors and Actuators B 78 (2001) 19-25, 7 pages.

Pan et al. "Self-Gating Effect Induced Large Performance Improvement of ZnO Nanocomb Gas Sensors" American Chemical Society, 2013, 7 pages.

Gergintschew et al. "The capacitatively controlled field effect transistor (CCFET) as a new low power gas sensor" Sensors and Actuators B 35-36 (1996) 285-589, 5 pages.

Lundstrom et al. "A hydrogen-sensitive MOS field-effect transistor" Appl. Phys. Lett. 26, 55 (1975), 4 pages.

* cited by examiner

GAS SENSITIVE FIELD EFFECT TRANSISTORS

CROSS REFERENCE TO RELATED APPLICATION

This is a nonprovisional claiming priority under 35 U.S.C. § 119 of U.S. Provisional Patent Application No. 62/763,340, filed on Jun. 13, 2018, entitled "Monolithic integrated gas-sensitive FETs in standard CMOS process." The prior application is incorporated by reference in its entirety.

TECHNICAL FIELD

The following description relates generally to sensors to detect gas types, gas concentrations, and gas mixtures, and methods of manufacturing and using the same.

BACKGROUND

A gas sensor is a device that can detect physical properties of gases, and subsequently output descriptive information, such as gas type and gas concentration. Many hazardous gases today may require monitoring, e.g., Hydrogen ($H_2$), nitrogen dioxide ($NO_2$) and benzene ($C_6H_6$), are common in urban environments as they originate from vehicles, furnaces, smoking, stoves, and various materials. These gases are flammable, toxic, or otherwise dangerous above certain critical concentrations. Exceeding critical concentrations may lead to fires, respiratory symptoms, dyspepsia and even cancers.

One existing class of gas sensors is the field effect transistor (FET) type gas sensor. Today's FET gas sensors rely on the use of special gate materials such as porous Palladioum (Pd) or special structures such as suspended control gates. Such requirements raise manufacturing costs and make compliance with industrial standards, miniaturization and batch processing more difficult. Today's FET gas sensors also have relatively high power consumption and low sensitivity at room temperature.

The above-described deficiencies of today's FET gas sensors are merely intended to provide an overview of some of problems of current technology, and are not intended to be exhaustive. Other problems with the state of the art, and corresponding benefits of some of the various non-limiting embodiments described herein, may become further apparent upon review of the following detailed description.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

DETAILED DESCRIPTION

Various aspects or features of this disclosure are described with reference to the drawings, wherein like reference numerals are used to refer to like elements throughout. In this specification, for purposes of explanation, numerous specific details are set forth in order to provide a thorough understanding of the subject disclosure. It should be understood, however, that certain aspects of this disclosure may be practiced without these specific details, or with other methods, components, materials, and so on. In other instances, well-known structures and devices are shown in block diagram form to facilitate describing the subject disclosure.

By way of introduction, the subject matter disclosed herein relates to as gas sensitive field effect transistor (FET) structures. The gas sensitive FET structures disclosed herein can include, inter alia, a body comprising a substrate layer, an intermediate layer over the substrate layer, and a passivation layer over the intermediate layer. Primary terminals disposed within the body can include at least one source terminal, at least one drain terminal and at least one gate terminal. A floating gate disposed within the body can comprise metal at a top surface of the intermediate layer. The passivation layer can be etched over the floating gate, and the floating gate can be electrically coupled to the gate terminal of the primary terminals. A sensing material layer comprising, e.g., zinc oxide (ZnO) nanorods or other other sensing materials, can be positioned over the floating gate. A reset element can be included for resetting the floating gate, and several example reset elements are disclosed herein.

In some embodiments, the reset element can include a lateral control gate disposed within the body, at the top surface of the intermediate layer and in a lateral position with respect to the floating gate. The passivation layer can be etched over the lateral control gate, as it is for the floating gate, and the sensing material layer can also be positioned over the lateral control gate. The lateral control gate can be operable to reset the floating gate, e.g., to a subthreshold region and/or to a strong inversion saturation region. The lateral control gate and the floating gate can optionally form an interdigitated electrode.

In further example embodiments, the reset element can include a reset switch disposed within the body. The reset switch can comprise a reset source terminal, a reset drain terminal and a reset gate terminal, and the floating gate can be electrically coupled to the reset switch. For example, the floating gate can be electrically coupled to the reset source terminal or the reset drain terminal. Furthermore, the reset source terminal or the reset drain terminal can be electrically coupled to a predetermined voltage as disclosed herein. The reset switch can be closable to set a voltage at the floating gate to the predetermined voltage, and the reset switch can be openable to return the floating gate to a floating state.

In still further example embodiments, gas sensitive FET structures can include multiple reset elements, e.g., a lateral control gate and a reset switch, as described further in connection with the accompanying figures.

In some implementations, the gas sensitive FET structures provided herein can optionally comprise a heater element in thermal contact with the body, and can optionally comprise a temperature sensor in thermal contact with the body. The heater element and temperature sensor can be used, e.g., to heat the gas sensitive FET structures to a desired temperature for improved gas sensitivity.

This disclosure furthermore provides a gas sensitive FET array, e.g., an array including gas sensitive FET structures disclosed herein. The gas sensitive FET array can include, for example, multiple gas sensitive FETs arranged adjacently on a substrate, wherein at least some of the multiple gas sensitive FETs include the gas sensitive FET structures provided herein. For example, the multiple gas sensitive FETs can comprise respective primary source terminals, respective primary drain terminals, respective primary gate terminals, and respective floating gates electrically coupled to the respective primary gate terminals. The respective floating gates can be coupled with respective reset elements, as disclosed herein. Passivation layers can be etched over the respective floating gates and sensing material layers can be disposed over the respective floating gates, as disclosed herein.

The gas sensitive FET structures of the array can be coupled together as disclosed herein. For example, the respective primary drain terminal of each of the multiple gas sensitive FETs can be coupled with a respective integration capacitor of multiple integration capacitors. The multiple gas sensitive FETs can be arranged in rows, and the multiple integration capacitors can be coupled with a row selection switch. An analog to digital converter can be electrically coupled to the row selection switch. In some embodiments, the multiple gas sensitive FETs comprise FETs of different types, and the FETs of different types can be arranged in columns so that columns of the gas sensitive FET array comprise gas sensitive FETs of a same type.

This disclosure furthermore provides methods of manufacturing and using the disclosed gas sensitive FET structures and the gas sensitive FET array. In some embodiments, the disclosed gas sensitive FET structures can be produced according to a complementary metal-oxide-semiconductor (CMOS) process adapted to include the elements provided herein, such as the floating gate and the reset elements. Methods of using the gas sensitive FET array can employ an electronic controller coupled with the gas sensitive FET array, to operate the gas sensitive FET array in order to detect ambient gas types and concentrations.

Figure 1:
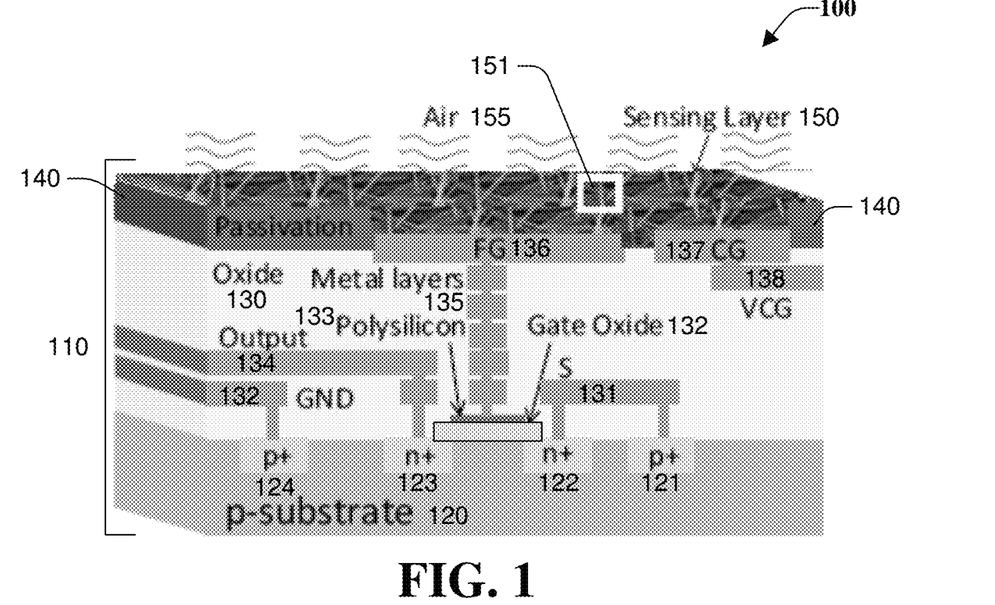
FIG. 1 provides a cross sectional view of an example gas sensitive FET structure with a lateral control gate, in accordance with one or more embodiments described herein.

FIG. 1 provides a cross sectional view of an example gas sensitive FET structure with a lateral control gate, in accordance with one or more embodiments described herein. Gas sensitive FET structure 100 includes a body 110 comprising a substrate layer (p-substrate 120), an intermediate layer (oxide 130) over the substrate layer 120, and a passivation layer 140 over the intermediate layer 130. Primary terminals disposed within the body 110 include at least one source terminal 131, at least one drain terminal (output 134) and at least one gate terminal (gate oxide 132 and polysilicon 133).

A floating gate (FG 136) disposed within the body 110 can comprise metal at a top surface of the intermediate layer 130. The floating gate 136 can be made of top metal in a CMOS process and may have an electrode of interdigitated shape. The number of fingers of the interdigitated electrode and the area of the electrode can vary as desired form particular embodiments. In some implementations, the floating gate 136 may be formed as continuous sheet of top metal, with any desired surface area.

The passivation layer 140 can be etched over the floating gate 136, and the floating gate 136 can be electrically coupled to the gate terminal (implemented via 132 and 133) of the primary terminals. A sensing material layer 150 can be positioned over the floating gate 146. A lateral control gate (implemented via 137 and 138) can be disposed within the body 110, at the top surface of the intermediate layer 130 and in a lateral position with respect to the floating gate 136. The lateral control gate 137, 138 can preset an operating point, that is, a sub-threshold operating region, of the gas sensitive FET structure 200.

Figure 4:
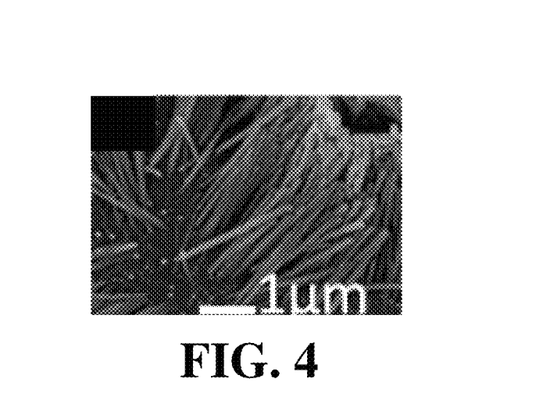
FIG. 4 provides a scanning electron microscope (SEM) image of an example sensing material layer, in accordance with one or more embodiments described herein.

FIG. 1 furthermore illustrates ambient air 155 over the sensing layer 150. A sensing layer portion 151 is indicated, and FIG. 4 provides a scanning electron micrograph (SEM) image of sensing layer portion 151. Metal layers 135 may be included in intermediate layer 130. The body 110 may include a ground terminal 132. The substrate layer 120 can include n and p doped portions 121, 122, 123, 124, as shown.

In an aspect with regard to FIG. 1, the lateral control gate implemented by 137, 138 and the floating gate 136 can form an interdigitated electrode (IDE). The gas sensitive FET structure 100 can operate in a weak-inversion region through coupling of the control gate voltage. The control gate can be optionally be made of other interconnect metal layers in a CMOS process, which places silicon oxide between the interconnect of floating gate 136 and the control gate 137. In a further aspect, the control gate 137 can comprise an electrode of any shape, and silicon oxide can be disposed between the floating gate 136 the control gate 137. Example control gate 137 shapes include straight line, spiral, and interdigitated electrode shapes with different finger numbers.

Figure 2:
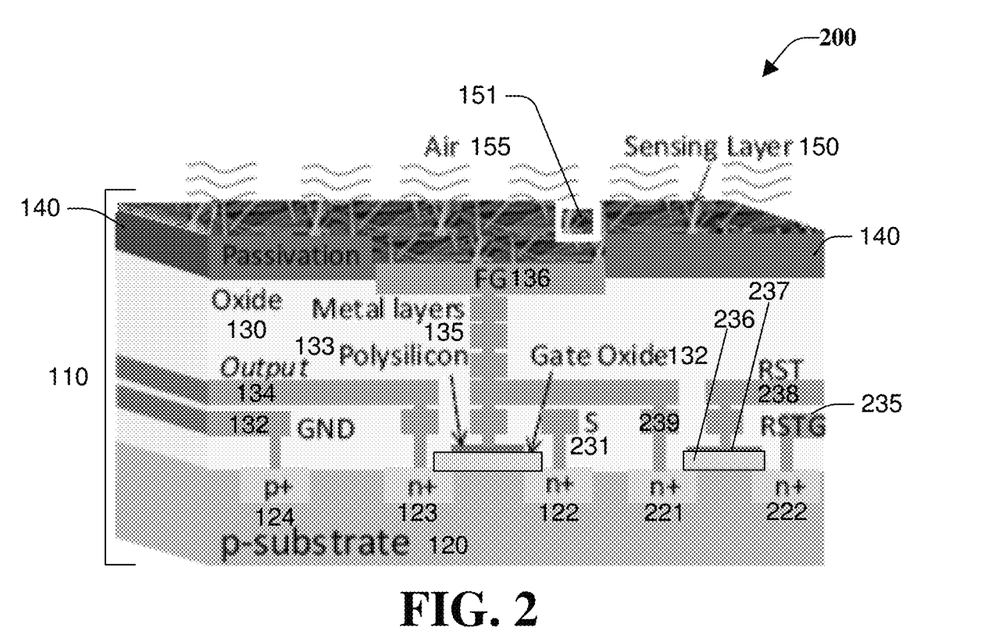
FIG. 2 provides a cross sectional view of an example gas sensitive FET structure with a reset switch, in accordance with one or more embodiments described herein.

FIG. 2 provides a cross sectional view of an example gas sensitive FET structure with a reset switch, in accordance with one or more embodiments described herein. Many of the elements of FIG. 2 are similar to those of FIG. 1, and like identifiers are used to indicate like elements. Gas sensitive FET structure 200 includes a body 110 comprising a substrate layer 120, an intermediate layer 130 over the substrate layer 120, and a passivation layer 140 over the intermediate layer 130. Primary terminals disposed within the body 110 include at least one source terminal 131, at least one drain terminal 134 and at least one gate terminal 132, 133. A floating gate 136 disposed within the body 110 can comprise metal at a top surface of the intermediate layer 130. The passivation layer 140 can be etched over the floating gate 136, and the floating gate 136 can be electrically coupled to the gate terminal 132, 133 of the primary terminals. A sensing material layer 150 can be positioned over the floating gate 146.

The lateral control gate 137, 138 is omitted from the embodiment illustrated in FIG. 2. Instead, FIG. 2 includes a reset switch disposed within the body 110. The reset switch comprises a reset source terminal 235, a reset drain terminal 239 and a reset gate terminal implemented by 236 and 237. The reset gate terminal 236, 237 is coupled with reset structure 238. In FIG. 2, the floating gate 136 is electrically coupled to the reset drain terminal 239. In other embodiments, the floating gate 136 can be electrically coupled to other elements of the reset switch. The reset source terminal 235 or the reset drain terminal 239 can be electrically coupled to a predetermined voltage. The reset switch can be closable to set a voltage at the floating gate 136 to the predetermined voltage, and the reset switch can be openable to return the floating gate 136 to a floating state.

FIG. 2 furthermore illustrates ambient air 155 over the sensing layer 150. A sensing layer portion 151 is indicated. Metal layers 135 may be included in intermediate layer 130. The body 110 may include a ground terminal 132. The substrate layer 120 can include n and p doped portions 122, 123, 124, 221 and 222, as shown.

In an aspect with regard to FIG. 2, the reset switch implemented by 235, 236, 237, 237 and 239 and the floating gate 136 can form an interdigitated electrode (IDE). The reset switch can be operable to preset an operating point, that is, a sub-threshold operating region, of the gas sensitive FET structure 200.

Figure 3:
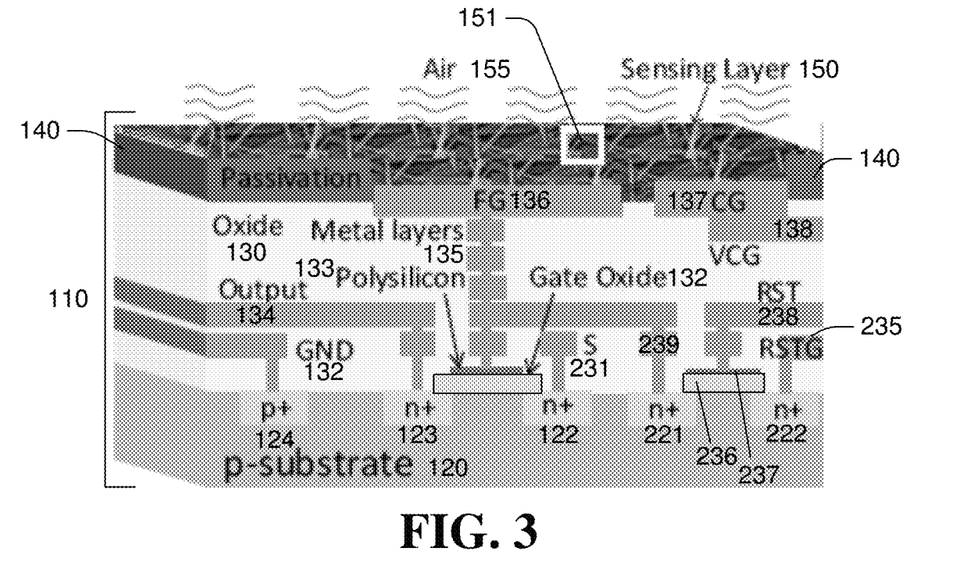
FIG. 3 provides a cross sectional view of an example gas sensitive FET structure with a lateral control gate and a reset switch, in accordance with one or more embodiments described herein.

FIG. 3 provides a cross sectional view of an example gas sensitive FET structure with a lateral control gate and a reset switch, in accordance with one or more embodiments described herein. Many of the elements of FIG. 3 are similar to those of FIG. 1 and FIG. 2, and like identifiers are used to indicate like elements. Gas sensitive FET structure 300 includes a body 110 comprising a substrate layer 120, an intermediate layer 130 over the substrate layer 120, and a passivation layer 140 over the intermediate layer 130. Primary terminals disposed within the body 110 include at least one source terminal 131, at least one drain terminal 134 and at least one gate terminal 132, 133. A floating gate 136 disposed within the body 110 can comprise metal at a top surface of the intermediate layer 130. The passivation layer 140 can be etched over the floating gate 136, and the floating gate 136 can be electrically coupled to the gate terminal 132, 133 of the primary terminals. A sensing material layer 150 can be positioned over the floating gate 146.

FIG. 3 includes a lateral control gate and a reset switch. As in FIG. 1, a lateral control gate 137, 138 can be disposed within the body 110, at the top surface of the intermediate layer 130 and in a lateral position with respect to the floating gate 136. As in FIG. 2, a reset switch disposed within the body 110 comprises a reset source terminal 235, a reset drain terminal 239 and a reset gate terminal implemented by 236 and 237. The reset gate terminal 236, 237 is coupled with reset structure 238. The floating gate 136 is electrically coupled to the reset drain terminal 239. In other embodiments, the floating gate 136 can be electrically coupled to other elements of the reset switch. The reset source terminal 235 or the reset drain terminal 239 can be electrically coupled to a predetermined voltage. The reset switch can be closable to set a voltage at the floating gate 136 to the predetermined voltage, and the reset switch can be openable to return the floating gate 136 to a floating state.

FIG. 3 furthermore illustrates ambient air 155 over the sensing layer 150. A sensing layer portion 151 is indicated. Metal layers 135 may be included in intermediate layer 130. The body 110 may include a ground terminal 132. The substrate layer 120 can include n and p doped portions 122, 123, 124, 221 and 222 e.g., as shown.

In an aspect of FIGS. 1-3, each of the illustrated gas sensitive FET structures 100, 200, 300 can comprise a floating gate 136 of exposed top metal connected to a metal-oxide-semiconductor field-effect transistor (MOSFET) polysilicon gate through other lower metal layers. Depending on the targeted application, various sensing materials can be deposited on top of the floating gate 136. When gas molecules in air 155 are absorbed by the sensing material layer 150, the work function at the surface will change, leading to a change in the threshold voltage of the gas sensitive FET structure 100, 200, or 300.

FIG. 4 provides a scanning electron microscope (SEM) image of an example sensing material layer, in accordance with one or more embodiments described herein. FIG. 4 provides an image of a sensing layer portion 151, e.g., as indicated in FIG. 1, FIG. 2, and FIG. 3. The image illustrates zinc oxide (ZnO) nanorods, as may be included in a sensing material layer in some embodiments.

This disclosure is not limited to any particular sensing material, and other materials may be used in other embodiments. Various kinds of sensing material can lead to charge transfer, band bending, or affinity change and can be deposited on top of the gas sensitive FET structures using various methods, including, e.g., pin coating, sputtering, spray, evaporation, drop coating, dip coating, inkjet printing, and pulsed laser deposition.

Figure 5:
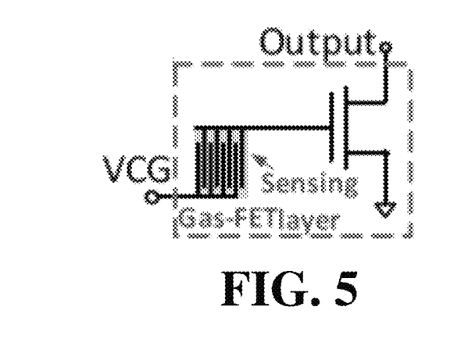
FIG. 5 illustrates an example circuit schematic for a circuit including a gas sensitive FET structure having a lateral control gate, in accordance with one or more embodiments described herein.

FIG. 5 illustrates an example circuit schematic for a circuit including a gas sensitive FET structure having a lateral control gate, in accordance with one or more embodiments described herein. The circuit schematic of FIG. 5 corresponds to the gas sensitive FET structure illustrated in FIG. 1. With reference to FIG. 5 and FIG. 1, a VCG connection point in FIG. 5 corresponds to VCG 138 for the lateral control gate in FIG. 1. A gas sensing FET layer in FIG. 5 corresponds to the sensing material layer 150 in FIG. 1. A FET element represented in FIG. 5 corresponds to the gas sensitive FET structure 100 in FIG. 1. An output in FIG. 5 corresponds to output 134 in FIG. 1.

Figure 6:
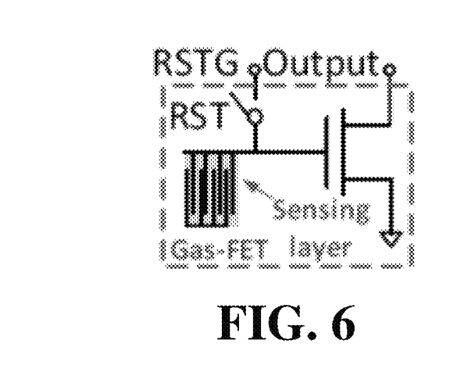
FIG. 6 illustrates an example circuit schematic for a circuit including a gas sensitive FET structure having a reset switch, in accordance with one or more embodiments described herein.

FIG. 6 illustrates an example circuit schematic for a circuit including a gas sensitive FET structure having a reset switch, in accordance with one or more embodiments described herein. The circuit schematic of FIG. 6 corresponds to the gas sensitive FET structure illustrated in FIG. 2. With reference to FIG. 6 and FIG. 2, a reset switch connection point (RSTG) in FIG. 6 corresponds to RSTG 235 for the reset switch illustrated in FIG. 2. A gas sensing FET layer in FIG. 6 corresponds to a sensing material layer 150 in FIG. 2. A FET element represented in FIG. 6 corresponds to the gas sensitive FET structure 200 in FIG. 2. An output in FIG. 6 corresponds to output 134 in FIG. 2.

Figure 7:
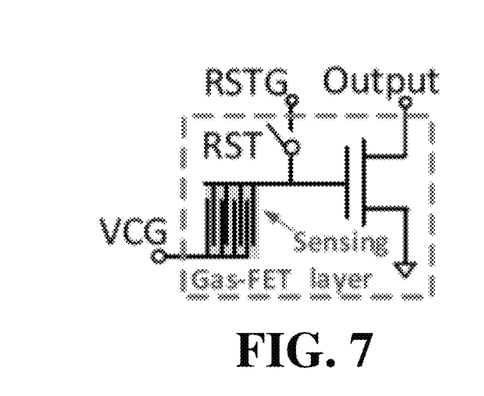
FIG. 7 illustrates an example circuit schematic for a circuit including a gas sensitive FET structure having a lateral control gate and a reset switch, in accordance with one or more embodiments described herein.

FIG. 7 illustrates an example circuit schematic for a circuit including a gas sensitive FET structure having a lateral control gate and a reset switch, in accordance with one or more embodiments described herein. The circuit schematic of FIG. 7 corresponds to the gas sensitive FET structure illustrated in FIG. 3. With reference to FIG. 7 and FIG. 3, a VCG connection point in FIG. 7 corresponds to VCG 138 for the lateral control gate illustrated in FIG. 3. A reset switch connection point (RSTG) in FIG. 7 corresponds to RSTG 235 for the reset switch illustrated in FIG. 3. A gas sensing FET layer in FIG. 7 corresponds to sensing material layer 150 in FIG. 3. A FET element represented in FIG. 7 corresponds to the gas sensitive FET structure 300 in FIG. 4. An output in FIG. 7 corresponds to output 134 in FIG. 3.

Figure 8:
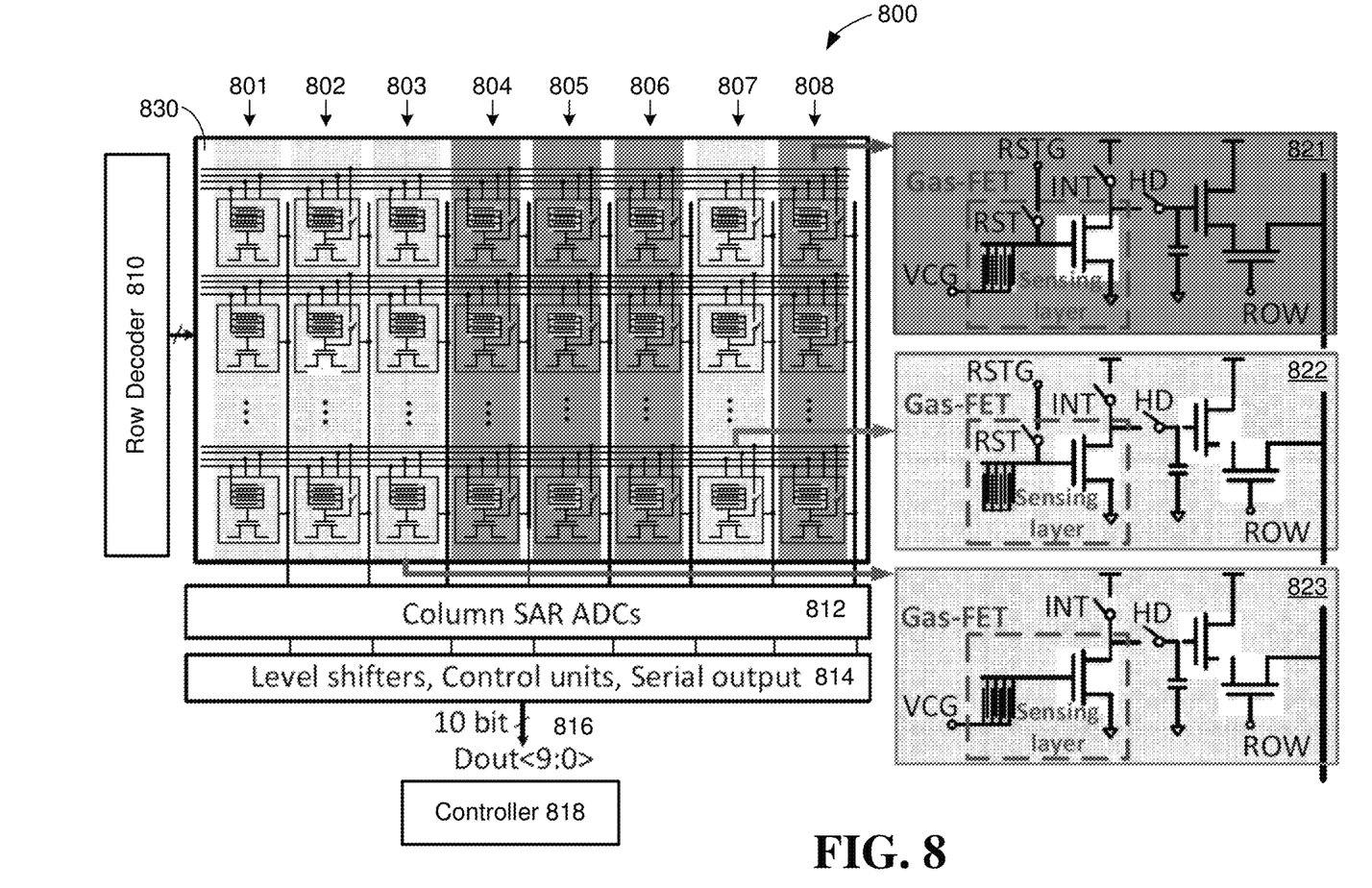
FIG. 8 illustrates an example gas sensitive FET array, in accordance with one or more embodiments described herein.

FIG. 8 illustrates an example gas sensitive FET array, in accordance with one or more embodiments described herein. Example gas sensitive FET array 800 includes multiple gas sensitive FETs arranged adjacently on a substrate 830. The gas sensitive FETs are arranged in columns 801, 802, 803, 804, 805, 806, 807, and 808. A row decoder 810 and column successive approximation register (SAR) analog to digital converters (ADCs) 812 are coupled with the multiple gas sensitive FETs. Level shifters, control units, and serial output 814 is coupled with the column SAR ADCs 812. An output 816 may be provided to a controller 818, and controller 818 can optionally also provide control outputs to the other illustrated elements of FIG. 8 in order to operate the gas sensitive FET array 800.

In FIG. 8, the gas sensitive FETs in columns 801, 802, 803, 804, 805, 806, 807, and 808 are each embedded within a readout component having a readout component type. The readout component types are illustrated at right, and include a lateral control gate and reset switch readout component type 821, a reset switch readout component type 822, and a lateral control gate readout component type 823. It will be appreciated that the lateral control gate and reset switch readout component type 821 includes a gas sensitive FET structure such as the gas sensitive FET structure 300 illustrated in FIG. 3. The reset switch readout component type 822 includes a gas sensitive FET structure such as the gas sensitive FET structure 200 illustrated in FIG. 2. The lateral control gate readout component type 823 includes a gas sensitive FET structure such as the gas sensitive FET structure 100 illustrated in FIG. 1. Furthermore, each column 801, 802, 803, 804, 805, 806, 807, and 808 may optionally include gas sensitive FETs of a same component type 821, 822, or 823.

Each of the readout component types 821, 822, and 823 may comprise an integration capacitor, the top plate of which can be connected to the drain of the gas sensitive FET structure, with bottom plate connected to ground, to integrate the drain source currents of the gas sensitive FET structures. A source follower and row selection switch or transmission gate can be connected to the top plates of the integration capacitors. A current source in each column 801, 802, 803, 804, 805, 806, 807, and 808 can be connected with the source followers in the same column. A column ADC of column SAR ADCs can be connected with the row selection switch or transmission gate output.

In an embodiment such as FIG. 8, the ability to control the operating points of the gas sensitive FET structures 100, 200, 300 and the dynamic subthreshold current readout of the sensor array 800 enables a dramatic reduction of the power consumption of the array 800.

In one example embodiment, an array 800 such as illustrated in FIG. 8 can be manufactured, e.g., using an 0.18 μm 1P6M CMOS process, in order to produce, e.g., a monolithic, fully integrated, high performance, high density 8×8 gas sensor array. The total chip size can be, e.g., around 1.61 mm×1.28 mm, with each Gas-FET occupying about 45 μm×46 μm. A selected sensing material such as ZnO can be deposited, e.g., using a programmable nanoliter injector.

In an example use of an array 800 such as illustrated in FIG. 8, the array 800 may be used to measure sub-ppm acetone for non-invasive diabetes diagnosis, through measurement of acetone concentration levels in human exhaled breath. Diabetes sufferers would exhibit concentration levels exceeding 1.7 ppm compared to levels below 0.8 ppm for healthy patients. Acetone responses from different gas sensitive FET array structures may be recorded and compared. Several measurement cycles may be performed at desired temperatures, e.g., room temperature.

Figure 9:
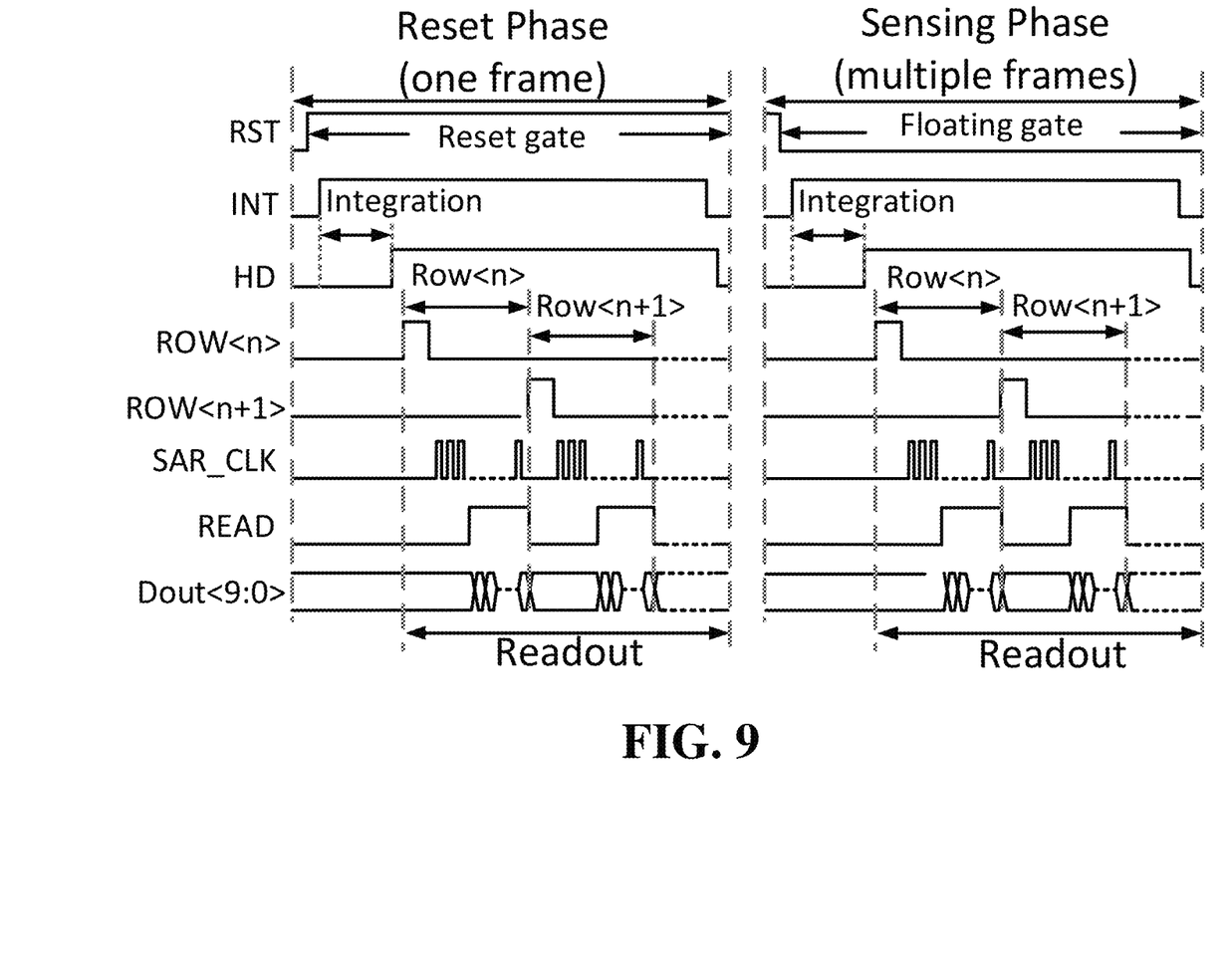
FIG. 9 provides a timing diagram for operation of a gas sensitive FET array, in accordance with one or more embodiments described herein.

FIG. 9 provides a timing diagram for operation of a gas sensitive FET array, in accordance with one or more embodiments described herein. FIG. 9 includes a reset phase and a sensing phase. In the reset phase, each gas sensitive FET structure in the array 800 can be biased (or reset) in the subthreshold region, with its drain current (an exponential function of its gas-dependent threshold voltage) being readout for maximum sensitivity. The sensing phase can be entered when reset switches are switched off and the gas sensitive FET structures of the array 800 are left floating. During a fixed integration time, drain currents of each of the gas sensitive FET structures of the array 800 discharge their pre-charged integration capacitors. A global shutter ensures that individual responses of gas sensitive FET structures of the array 800 are captured at a same time. After global sensing current integration, voltage on integration capacitors can be selected by row decoders (such as row decoder 810 in FIG. 8) and transferred to column SAR ADCs 812 using source followers. Digital codes can then be serially shifted out, as output 816.

The timing diagram in FIG. 9 illustrates operation of the reset signal (RST) for control of the reset phase or the sensing phase. The signals INT and HD control signal current integration time. After a global current integration and storage on the integration capacitors, the column SAR ADCs 812 quantize the stored voltage in each row sequentially by the row decoder signal ROW<n> to ROW<n+1>. The gated SAR_CLK signal controls the SAR logic in the column ADCs 812. After the quantization of each row, the digital output code is ready to be readout, which is indicated by a read ready signal READ, meanwhile, the digital output code Dout<9:0> is shifted out in serial.

Figure 10:
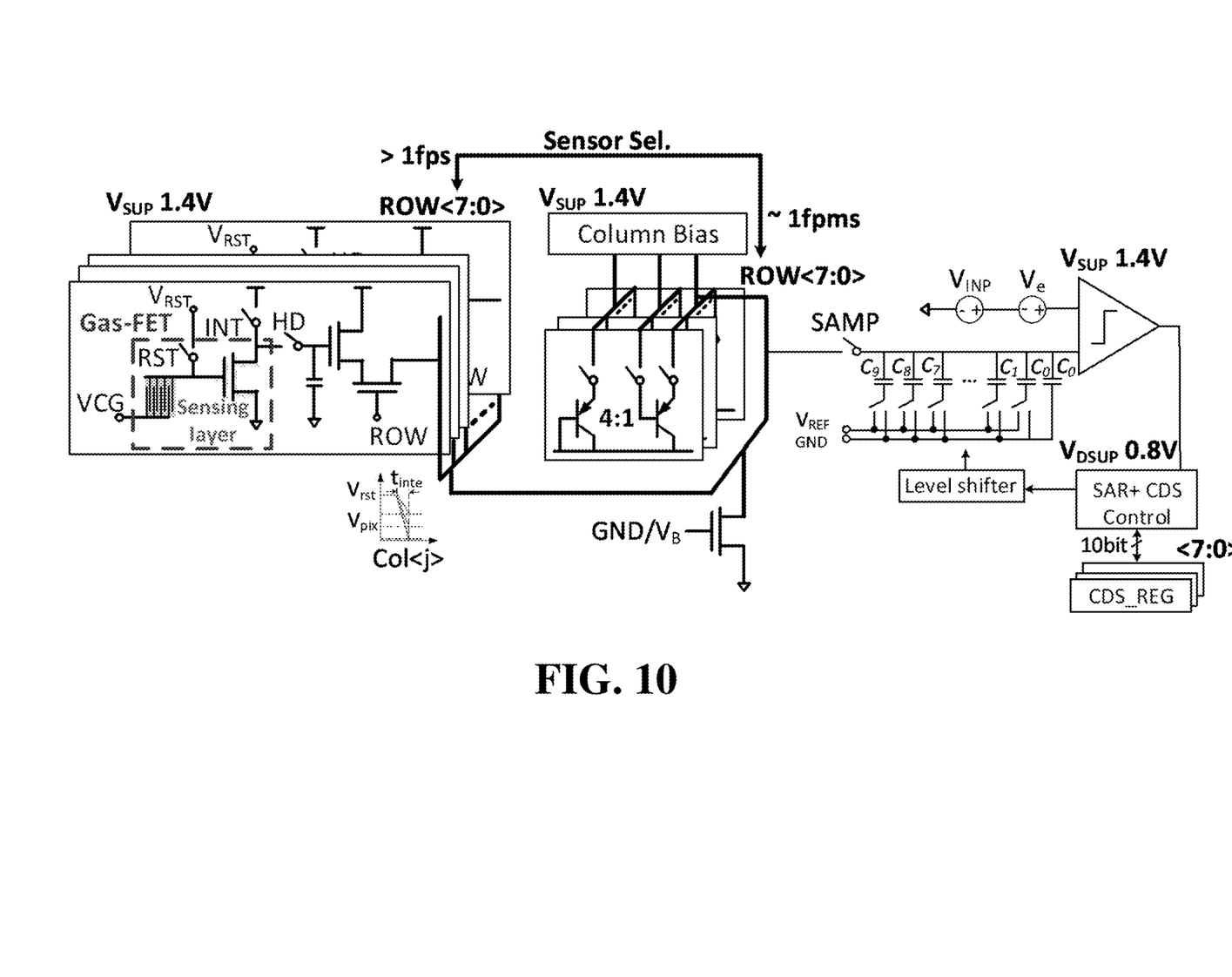
FIG. 10 illustrates an example structure including embedded heaters and temperature sensors, in accordance with one or more embodiments described herein.

FIG. 10 illustrates an example structure including embedded heaters and temperature sensors, in accordance with one or more embodiments described herein. In FIG. 10, heater elements comprising a polysilicon layer or an interconnect metal layer can be formed in a spiral, square, or straight shape. The heater elements may be employed for temperature modulation of the sensor array 800 to build a more diverse pattern database for gas classification. Temperature sensors can be positioned, e.g., under each exposed top metal sensing area, a small distance beneath each exposed top metal sensing area. Temperature sensors can sense temperatures at different gas sensitive FET structures in an array 800 for use in controlling temperature modulation by the heater elements, and for temperature calibration.

FIG. 10 illustrates one example column of readout circuits for a gas sensitive FET structure and temperature sensors. A sensor selection signal can select to readout the FET signal or the temperature sensor signal. In the FET signal readout mode, the current bias of the source followers is turned on, and the integrated signal on the capacitors will be connected to the column SAR ADCs by the row decoder signal ROW<7:0>.

In the temperature sensor readout mode, the current bias of the source followers is turned off, and the voltage output of the temperature sensor core, comprising two core BJTs in 4:1 area ratio, can be connected to the column SAR ADCs sequentially by the control of the row decoder ROW<7:0>. The core BJTs in each sensing element can share the same bias circuits in the same column. The SAR ADC in each column contains a capacitor array, a comparator, and Correlated Double Sampling (CDS) control unit to perform CDS in the mixed signal domain by the pre-load of the previous quantized digital code to the bottom plate of the capacitors array. A group of level shifters can be used to shift the digital voltage of 0.8V to higher voltage in analog domains of 1.4V or higher.

Figure 11:
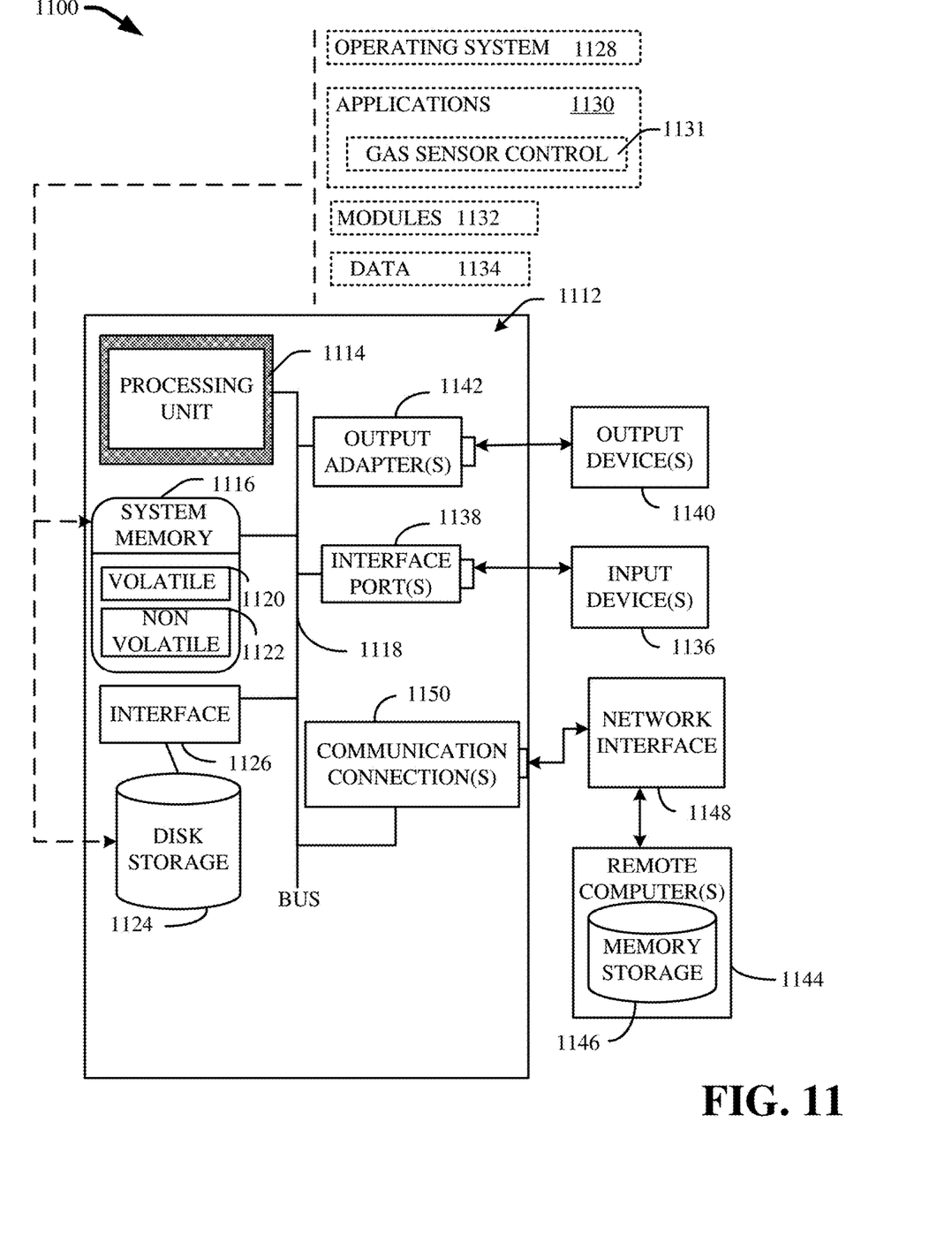
FIG. 11 is an example computing device which can serve as an electronic controller for a gas sensitive FET array, in accordance with one or more embodiments described herein.

FIG. 11 is an example computing device which can serve as a controller for the gas sensitive FET array, in accordance with one or more embodiments described herein. In general, the techniques described herein associated with electronic controller 818 can be applied to any device or set of devices (machines) capable of running programs and processes. It can be understood, therefore, that wearable devices, mobile devices, servers including physical and/or virtual machines, personal computers, laptops, handheld, portable and other computing devices and computing objects of all kinds including cell phones, tablet/slate computers, gaming/entertainment consoles and the like can be used in connection with various implementations including those exemplified herein. Accordingly, the general purpose computing mechanism described below with reference to FIG. 11 is but one example of a computing device.

In order to provide a context for the various aspects of the disclosed subject matter, FIG. 11 and the following discussion, are intended to provide a brief, general description of a suitable environment in which the various aspects of the disclosed subject matter can be implemented. While subject matter has been described herein in the general context of computer-executable instructions of a computer program that runs on a computer and/or computers, those skilled in the art will recognize that the disclosed subject matter also can be implemented in combination with other program modules. Generally, program modules include routines, programs, components, data structures, etc. that perform particular tasks and/or implement particular abstract data types.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory, by way of illustration, and not limitation, volatile memory 1120, non-volatile memory 1122, disk storage 1124, solid-state memory devices, and memory storage 1146. Further, non-volatile memory can be included in read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, including single-processor or multiprocessor computer systems, mini-computing devices, mainframe computers, as well as personal computers, hand-held computing devices (e.g., PDA, phone, watch, tablet computers, netbook computers, . . . ), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

FIG. 11 illustrates a block diagram of a computing system 1100, e.g., configured to operate as a controller 818, and operable to execute the disclosed systems and methods in accordance with an embodiment. Computer 1112, which can be, for example, part of the hardware of system 1100, includes a processing unit 1114, a system memory 1116, and a system bus 1118. System bus 1118 couples system components including, but not limited to, system memory 1116 to processing unit 1114. Processing unit 1114 can be any of various available processors. Dual microprocessors and other multiprocessor architectures also can be employed as processing unit 1114.

System bus 1118 can be any of several types of bus structure(s) including a memory bus or a memory controller, a peripheral bus or an external bus, and/or a local bus using any variety of available bus architectures including, but not limited to, Industrial Standard Architecture (ISA), Micro-Channel Architecture (MSA), Extended ISA (EISA), Intelligent Drive Electronics, VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1494), and Small Computer Systems Interface (SCSI).

System memory 1116 can include volatile memory 1120 and nonvolatile memory 1122. A basic input/output system (BIOS), containing routines to transfer information between elements within computer 1112, such as during start-up, can be stored in nonvolatile memory 1122. By way of illustration, and not limitation, nonvolatile memory 1122 can include ROM, PROM, EPROM, EEPROM, or flash memory. Volatile memory 1120 includes RAM, which acts as external cache memory. By way of illustration and not limitation, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1112 can also include removable/non-removable, volatile/non-volatile computer storage media. FIG. 11 illustrates, for example, disk storage 1124. Disk storage 1124 includes, but is not limited to, devices like a magnetic disk drive, floppy disk drive, tape drive, flash memory card, or memory stick. In addition, disk storage 1124 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1124 to system bus 1118, a removable or non-removable interface is typically used, such as interface 1126.

Computing devices typically include a variety of media, which can include computer-readable storage media or communications media, which two terms are used herein differently from one another as follows.

Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD ROM, digital versatile disk (DVD) or other optical disk storage, magnetic cassettes, magnetic tape, magnetic disk storage or other magnetic storage devices, or other tangible media which can be used to store desired information. In this regard, the term "tangible" herein as may be applied to storage, memory or computer-readable media, is to be understood to exclude only propagating intangible signals per se as a modifier and does not relinquish coverage of all standard storage, memory or computer-readable media that are not only propagating intangible signals per se. In an aspect, tangible media can include non-transitory media wherein the term "non-transitory" herein as may be applied to storage, memory or computer-readable media, is to be understood to exclude only propagating transitory signals per se as a modifier and does not relinquish coverage of all standard storage, memory or computer-readable media that are not only propagating transitory signals per se. For the avoidance of doubt, the term "computer-readable storage device" is used and defined herein to exclude transitory media. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

It can be noted that FIG. 11 describes software that acts as an intermediary between users and computer resources described in suitable operating environment 1100. Such software includes an operating system 1128. Operating system 1128, which can be stored on disk storage 1124, acts to control and allocate resources of computer system 1112. It is to be noted that the disclosed subject matter can be implemented with various operating systems or combinations of operating systems.

System applications 1130 take advantage of the management of resources by operating system 1128 through program modules 1132 and program data 1134 stored either in system memory 1116 or on disk storage 1124. In some embodiments, a gas sensor control application 1131 may control operations described in connection with FIG. 11 in order to perform gas sensor measurements and to identify gasses or gas concentrations under measurement. Gas sensor control application 1131 can control measurements using the components of the gas sensitive FET array, as described herein, and can record measurement data as data 1134.

A user can enter commands or information into computer 1112 through input device(s) 1136, including via fingertip pointing as described herein. As an example, a mobile device and/or a portable device can include a user interface embodied in a touch sensitive display panel allowing a user to interact with computer 1112. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, cell phone, smartphone, tablet computer, etc. These and other input devices connect to processing unit 1114 through system bus 1118 by way of interface port(s) 1138. Interface port(s) 1138 include, for example, a serial port, a parallel port, a game port, a universal serial bus (USB), an infrared port, a Bluetooth port, an IP port, or a logical port associated with a wireless service, etc. Output device(s) 1140 use some of the same type of ports as input device(s) 1136.

Thus, for example, a USB port can be used to provide input to computer 1112 and to output information from computer 1112 to an output device 1140. Output adapter 1142 is provided to illustrate that there are some output devices 1140 like monitors, speakers, and printers, among other output devices 1140, which use special adapters. Output adapters 1142 include, by way of illustration and not limitation, video and sound cards that provide means of connection between output device 1140 and system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. Remote computer(s) 1144 can be a personal computer, a server, a router, a network PC, cloud storage, cloud service, a workstation, a microprocessor based appliance, a peer device, or other common network node and the like, and typically includes many or all of the elements described relative to computer 1112.

For purposes of brevity, only a memory storage device 1146 is illustrated with remote computer(s) 1144. Remote computer(s) 1144 is logically connected to computer 1112 through a network interface 1148 and then physically connected by way of communication connection 1150. Network interface 1148 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit-switching networks like Integrated Services Digital Networks (ISDN) and variations thereon, packet switching networks, and Digital Subscriber Lines (DSL). As noted below, wireless technologies may be used in addition to or in place of the foregoing.

Communication connection(s) 1150 refer(s) to hardware/software employed to connect network interface 1148 to bus 1118. While communication connection 1150 is shown for illustrative clarity inside computer 1112, it can also be external to computer 1112. The hardware/software for connection to network interface 1148 can include, for example, internal and external technologies such as modems, including regular telephone grade modems, cable modems and DSL modems, ISDN adapters, and Ethernet cards.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media, device readable storage devices, or machine readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

While the invention is susceptible to various modifications and alternative constructions, certain illustrated implementations thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

In addition to the various implementations described herein, it is to be understood that other similar implementations can be used or modifications and additions can be made to the described implementation(s) for performing the same or equivalent function of the corresponding implementation(s) without deviating therefrom. Accordingly, the invention is not to be limited to any single implementation, but rather is to be construed in breadth, spirit and scope in accordance with the appended claims.

What is claimed is:

1. A gas sensitive field effect transistor (FET) structure, comprising:
   a body comprising a substrate layer, an intermediate layer over the substrate layer, and a passivation layer over the intermediate layer, primary terminals disposed within the body;
   the primary terminals comprising at least one source terminal, at least one drain terminal and at least one gate terminal;
   a floating gate disposed within the body, the floating gate comprising metal at a top surface of the intermediate layer, wherein the passivation layer has been etched to form an open area exposing the floating gate, and wherein the floating gate is electrically coupled to the at least one gate terminal via multiple metal layers and a polysilicon layer in contact with the at least one gate terminal;
   a lateral control gate disposed within the body, at the top surface of the intermediate layer in a lateral position with respect to the floating gate, wherein the open area exposes the lateral control gate; and
   a sensing material layer positioned in the open area on the floating gate and the lateral control gate.

2. The gas sensitive FET structure of claim 1, wherein the sensing material layer comprises zinc oxide (ZnO) nanorods.

3. The gas sensitive FET structure of claim 1, wherein the lateral control gate is operable to reset the floating gate to a subthreshold region.

4. The gas sensitive FET structure of claim 1, wherein the lateral control gate is operable to reset the floating gate to a strong inversion saturation region.

5. The gas sensitive FET structure of claim 1, wherein the lateral control gate and the floating gate form an interdigitated electrode.

6. The gas sensitive FET structure of claim 1, wherein the gas sensitive FET structure is produced according to a complementary metal-oxide-semiconductor (CMOS) process.

7. The gas sensitive FET structure of claim 1, further comprising a heater element comprising a polysilicon layer or an interconnect metal layer in thermal contact with the body.

8. The gas sensitive FET structure of claim 1, further comprising a temperature sensor positioned under the passivation layer.

9. A gas sensitive field effect transistor (FET) structure, comprising:
a body comprising a substrate layer, an intermediate layer, and a passivation layer;
primary terminals disposed within the body, the primary terminals comprising a gate terminal;
a floating gate disposed within the body, the floating gate comprising metal at a top surface of the intermediate layer, wherein the passivation layer has been etched to form an open area exposing the floating gate, and wherein the floating gate is electrically coupled to the gate terminal via multiple metal layers and a polysilicon layer in contact with the gate terminal;
a lateral control gate disposed within the body in a lateral position with respect to the floating gate, wherein the open area exposes the lateral control gate; and a sensing material layer positioned in the open area on the floating gate and the lateral control gate.

10. The gas sensitive FET structure of claim 9, wherein the sensing material layer comprises zinc oxide (ZnO) nanorods.

11. The gas sensitive FET structure of claim 9, wherein the lateral control gate is operable to reset the floating gate to a subthreshold region.

12. The gas sensitive FET structure of claim 9, wherein the lateral control gate is operable to reset the floating gate to a strong inversion saturation region.

13. The gas sensitive FET structure of claim 9, further comprising a heater element comprising a polysilicon layer or an interconnect metal layer in thermal contact with the body.

14. The gas sensitive FET structure of claim 9, further comprising a temperature sensor positioned under the passivation layer.

15. A gas sensitive field effect transistor (FET) structure, comprising:
a substrate layer, an intermediate layer over the substrate layer, and a passivation layer over the intermediate layer;
primary terminals comprising at least one source terminal, at least one drain terminal and at least one gate terminal;
a floating gate comprising metal at a top surface of the intermediate layer, wherein the passivation layer has been etched over to form an open area exposing the floating gate, and wherein the floating gate is electrically coupled to the at least one gate terminal via multiple metal layers disposed underneath the floating gate;
a lateral control gate, at the top surface of the intermediate layer in a lateral position with respect to the floating gate, wherein the open area exposes the lateral control gate; and
a sensing material layer positioned in the open on the floating gate and the lateral control gate.

16. The gas sensitive FET structure of claim 15, wherein the sensing material layer comprises zinc oxide (ZnO) nanorods.

17. The gas sensitive FET structure of claim 15, wherein the lateral control gate is operable to reset the floating gate to a subthreshold region.

18. The gas sensitive FET structure of claim 15, wherein the lateral control gate is operable to reset the floating gate to a strong inversion saturation region.

19. The gas sensitive FET structure of claim 15, further comprising a heater element comprising a polysilicon layer or an interconnect metal layer in thermal contact with the substrate layer or the intermediate layer.

20. The gas sensitive FET structure of claim 15, further comprising a temperature sensor positioned under the passivation layer.

* * * * *